United States Patent [19]
Williams

[11] Patent Number: 5,858,739
[45] Date of Patent: Jan. 12, 1999

[54] GAS SENSOR

[75] Inventor: David Edward Williams, Abingdon, United Kingdom

[73] Assignee: Capteur Sensors & Analysers, Ltd., United Kingdom

[21] Appl. No.: 884,442

[22] Filed: Jun. 27, 1997

Related U.S. Application Data

[63] Continuation-in-part of Ser. No. 621,901, Mar. 26, 1996, abandoned, which is a continuation of Ser. No. 150,046, filed as PCT/GB92/00897, May 18, 1992, abandoned.

[30] Foreign Application Priority Data

May 18, 1991 [GB] United Kingdom .................... 9110797

[51] Int. Cl.[6] ........................ G01N 27/04; G01N 27/416
[52] U.S. Cl. ........................ 436/151; 73/31.05; 204/412; 204/427; 422/90; 422/94; 422/98; 436/152
[58] Field of Search .............................. 73/31.05, 31.06; 422/90, 94, 98; 436/151, 152; 204/412, 427

[56] References Cited

U.S. PATENT DOCUMENTS

| 3,558,280 | 1/1971 | Panson et al. .................... 73/31.05 |
| 3,901,067 | 8/1975 | Boardman, Jr. et al. ............. 422/98 X |
| 4,099,922 | 7/1978 | Yasuda et al. .................... 422/95 |
| 4,206,173 | 6/1980 | Yamaguchi et al. ................ 422/98 |
| 4,277,439 | 7/1981 | Yasuda et al. .................... 422/94 |
| 4,287,751 | 9/1981 | Yasuda et al. .................... 73/23 |
| 4,327,051 | 4/1982 | Yasuda et al. .................... 422/98 X |
| 4,450,428 | 5/1984 | Ohta et al. ...................... 422/98 X |
| 4,453,397 | 6/1984 | Ohta et al. ...................... 73/23 |
| 4,913,792 | 4/1990 | Nagata et al. .................... 204/412 |
| 4,953,387 | 9/1990 | Johnson et al. ................... 422/98 X |

OTHER PUBLICATIONS

E. F. Hasler et al. *Chem. Abstr.* 1978, 89, 148531g.

*Primary Examiner*—Arlen Soderquist
*Attorney, Agent, or Firm*—James B. Middleton

[57] ABSTRACT

A method for determining the presence of a first gas in a second gas uses a gas sensor made up of at least two pairs of electrodes, each pair of electrodes having different spacing between the electrodes. The electrodes of the gas sensor have surfaces that are reactive to the gases under investigation. The gas sensor is exposed to the gases, and the electrical resistances between the pairs of electrodes are measured over a period of time. 'The results are compared with a calibration curve to determine if the first gas is present in the second, and to determine of the sensor is malfunctioning.

11 Claims, 5 Drawing Sheets

GAS SENSOR

CROSS-REFERENCE TO RELATED APPLICATIONS

This application is a continuation-in-part of the application by the same inventor, titled "A Gas Sensor", filed on Mar. 26, 1996, and having application Ser. No. 08/621,901, now abandoned, which is a continuation of the application by the same inventor titled "Gas Sensor", filed Mar. 30, 1994, having application Ser. No. 08/150,046, now abandoned, the last named application being the National Stage of the PCT application titled "A Gas Sensor", filed 18 May 1992, having Application No. PCT/GB/00897, and claiming priority in the British application No. 91 10797.9, filed 18 May 1991.

BACKGROUND OF THE INVENTION

1. Field of the Invention

This invention relates to methods for detecting at least one gaseous medium in the presence of at least one other gaseous medium, and to gas sensors suitable for use in such methods.

2. Discussion of the Prior Art

It is well known that the electrical conductivities of metal oxide semiconducting materials are sensitive to the presence of various gases or vapors and can be used in sensors to detect their presence. See for example the documents GB-A-2 149 120; GB-A-2 149 121; GB-A-2 149 122; GB-A-2 149 123; GB-A-2 166 244 and GB-A-2 218 523, and papers "The Tin Oxide Gas Sensor and its applications", J. Watson, Sensors and Actuators 54(1984) 29–42; "The Detection and Measurement of CO using ZnO Single Crystals", B. Bott et al., Sensors and Actuators 5(1984) 65–73; "The Role of Catalysis in Solid State Gas Sensors", S. J. Gentry et al, Sensors and Actuators 10(1986) 141–163; "Selectivity in Actuators 12(1987) 425–440; and "Electrical Conduction in Solid State Gas Sensors", J. W. Gardner, Sensors and Actuators 18(1989) 373–387.

All such gas sensors rely on the gaseous medium under observation impinging on a surface of a body of the semiconducting metal oxide material and then undergoing some reaction with it which affects the conductance of the semiconducting metal oxide material, which is detected by means of at least one pair of electrodes which are formed upon the body of semiconducting metal oxide material. Hence their performance can be affected by the presence of substances, gaseous or otherwise (other than the materials to be detected), that affect the surface chemistry of the body of semiconducting metal oxide material. It is important to be able to detect when such spurious effects are occurring.

SUMMARY OF THE INVENTION

The present invention is based upon the fact that, in a perfectly operating sensor, at a given temperature the ratio of the resistance between a first pair of electrodes which form part of the sensor and that between a second pair of electrodes, which also form part of the sensor, but which have a different separation than that between the first pair of electrodes, should vary in a consistent way as a function of the concentration of one gaseous medium, to which the sensor material is adapted to respond, when in the presence of another.

If, however, any changes occur in the surface chemistry of the sensor body (which may or may not be of semiconducting metal oxide material, and which carries the electrodes), such as may be caused by poisoning material, then the ratio of the two resistances corresponding to various compositions of the gaseous mixture will no longer vary in the same way as before. Hence by making continuous measurements of the ratio of the resistances between the two sets of electrodes and comparing the changes in the ratio of the resistances with a calibration curve, one can distinguish between changes due to real changes in the composition of the gaseous medium under observation and spurious changes due to changes in the performance of the sensor.

According to the invention in a first aspect, therefore, a gas sensor, for determining the presence of a first gaseous medium in a second gaseous medium, is characterized by: a body of an electrically conductive material having an electrical conductivity sensitive to the presence of the first gaseous medium in the second gaseous medium, electrodes disposed in sets on the said body and comprising at least a first set and a second set, the distance between the electrodes of a set of electrodes, or the relationship between the electrodes of a set and an active surface of the said body, being different in the case of each said set, and means for determining the relationship between the resistance between the electrodes in the first set and that between the electrodes in the second set, so that the composition of the gaseous mixture comprising the said media can be determined from that relationship.

Preferably there is an electrode common to more than one set.

The sensor may be constructed in various different ways. It may for example be a planar or a cylindrical configuration.

In a preferred embodiment of the invention, the pair of electrodes used include a common electrode situated asymmetrically in relation to an electrode of one set and an electrode of another set. This arrangement is for example applicable to both the planar and the cylindrical form of the sensor.

In another arrangement, the electrically conductive body is in the form of a porous disc with a common electrode formed over one planar surface, a central disc electrode on the other planar surface of the disc and an annular electrode surrounding the central disc electrode and concentric with it.

A preferred material for use in the present invention comprises a semiconducting metal oxide ceramic material, which may be in the form of a single such oxide or a mixture of such oxides. Examples of such oxides are tin (IV) oxide, zinc oxide, tungsten (VI) oxide and oxides described in U.K. patent specifications Nos. GB-A-2 149 120; GB-A-2 149 121; GB-A-2 149 122; GB-A-2 149 123; GB-A-2 166 244. The above oxides can be made to be catalytic for a combustion reaction for use in the performance of the present invention by providing a thin surface coating of particles of one of the well-known catalytic metals such at Pt or Pd; alternatively, they can be made to be catalytic for a decomposition reaction by providing a coating of a suitable material. A decomposition catalyst may be chosen that is specific to a selected gas. Also, the semiconducting metal oxide material can be chosen to be sensitive to a decomposition product of a selected gas.

According to the invention in a second aspect, a method for determining, in a gaseous mixture, the presence of a first gaseous medium in a second gaseous medium, is characterized by the operations of 1. Exposing to the second gaseous medium an active surface of the body of a gas sensor according to the invention in its first aspect;
2. Measuring as a function of time the electrical resistances between a pair of electrodes of the first set and between a pair of electrodes of the second set of the sensor; and, 3. Using the measured values of the said resistances to compare the relationship between them with a calibration curve indicative of variation of the ratio between the said resistances with concentration of the first gaseous medium in the second gaseous medium, whereby to determine the composition of the gaseous mixture and to detect malfunction of the sensor.

Examples of gases the presence of which may be detected by the present invention include hydrocarbons such as methane, ethane, propane, butane, ethylene, benzene and toluene; carbon monoxide; hydrogen; ammonia; hydrogen sulfide; nitrogen dioxide; sulfur dioxide; alcohol vapors such as those of methanol and ethanol; and aldehyde and ketone vapors such as those of formaldehyde, acetone and methyl ethyl ketone.

BRIEF DESCRIPTION OF THE DRAWINGS

Embodiments of the invention will now be described, by way of example only and with reference to the accompanying drawings, in which.

DETAILED DESCRIPTION OF THE EMBODIMENTS

Figure 1A:
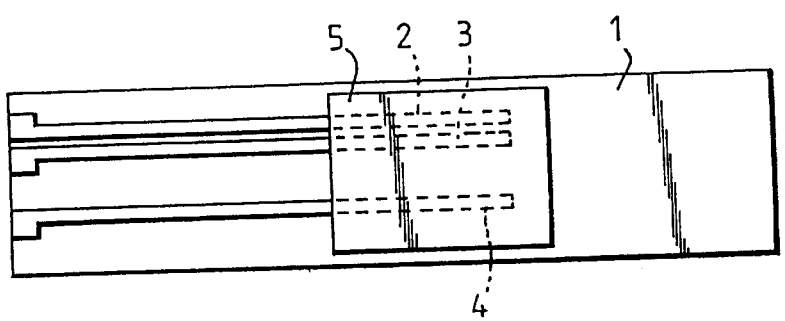
FIG. 1 is in two parts denoted (a) and (b), which are a plan view and a cross-sectional view, respectively, of a gas sensor in a first embodiment of the invention.
Figure 1B:
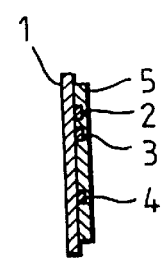

The sensor shown in FIG. 1 consists of a gas-impermeable substrate 1 such as a piece of alumina, upon which are deposited three electrodes 2, 3 and 4. These constitute two sets of electrodes 2, 3 and 3, 4, the electrode 3 is asymmetrical with respect to the electrodes 2 and 4, i.e. it is closer to the electrode 2 than to the electrode 4. A body of semiconducting metal oxide material partly covers the electrodes 2, 3, and 4 and constitutes a sensing element 5. The sensing element 5 is porous and has an electrical conductivity which is sensitive to a gas to be detected by the sensor. Its outer surface is active, i.e. exposed to the gaseous environment. If necessary a catalytic layer, not shown, can be deposited on the sensing element 5 to ensure that this gas either burns or is decomposed, so as to cause a change to occur in the conductivity of the sensing element 5.

Figure 2A:
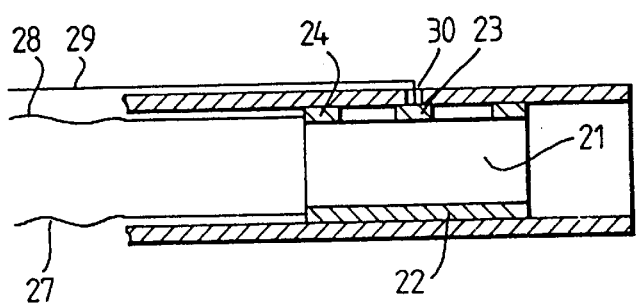
FIG. 2 is again in two parts denoted (a) and (b), which are a cross sectional view and a plan view, respectively, of a gas sensor in a second embodiment of the invention.
Figure 2B:
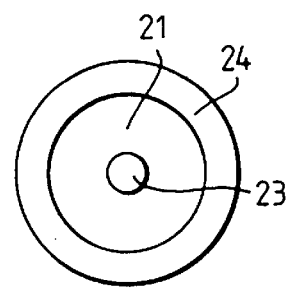

In the sensor shown in FIG. 2, the sensing element is in the form of a disc 21 of porous semiconducting metal oxide material. A metal electrode 22 covers one flat face of the sensing element 21. On the other flat face of the sensing element 21, a central disc electrode 23 and an annular outer electrode 24 are arranged coaxially. The sensing element 21, together with its electrodes 22, 23 and 24, are sandwiched between two flat, parallel, impervious insulating tiles. Contact leads 27 and 28 are attached to the edges of the electrodes 22 and 24 respectively, and a further lead 29 is attached to the electrode 23 via a hole 30 in the corresponding tile. The active surface of the element 21 is here its outer cylindrical surface, which is exposed.

In FIG. 2, it can be seen that the relationship between the set of electrodes 22, 23 and the reactive surface is different from that between the set of electrodes 22, 24 and the same surface, and that the electrode 24 is close to the latter, whereas the electrode 23 is as far away from it as is possible with this configuration.

Figure 3:
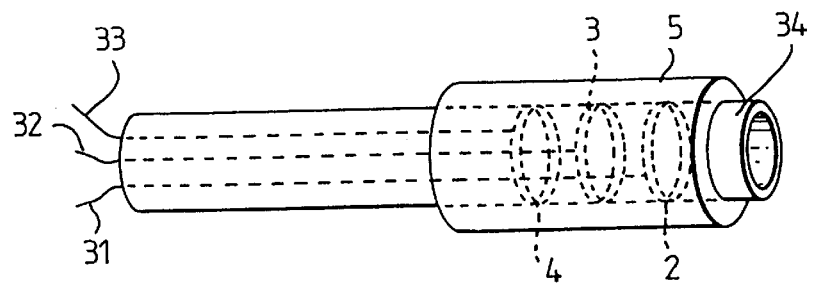
FIG. 3 is a general view of a gas sensor in a third embodiment of the invention.

FIG. 3 shows a sensor of tubular geometry, but in other respects it is similar to the sensor of FIG. 1. In FIGS. 1 and 3, corresponding elements have corresponding reference numerals. It should be noted that, in practice, the common electrode 3 is closer to one of the electrodes 2, 4 than to the other. Contact with the electrodes 2, 3 and 4 in FIG. 3 is made via leads 31, 32 and 33 respectively, which run inside the tubular substrate 34, the outer surfaces of which are active.

In describing the operation of such devices, it is necessary to introduce two parameters Kp and KT. Kp is a measure of the sensitivity of the material of the sensing element to a given gas and hence the concentration of that gas in a gaseous medium under test. KT is a measure of the reactivity and the rate of diffusion, through the sensing element, of the gas or of products of its combustion or decomposition. KT is a function of the operating temperature of the sensor, and this gives the opportunity to use one sensor for the detection of different gases in a mixture by varying the operating temperature of the sensor.

Figure 4:
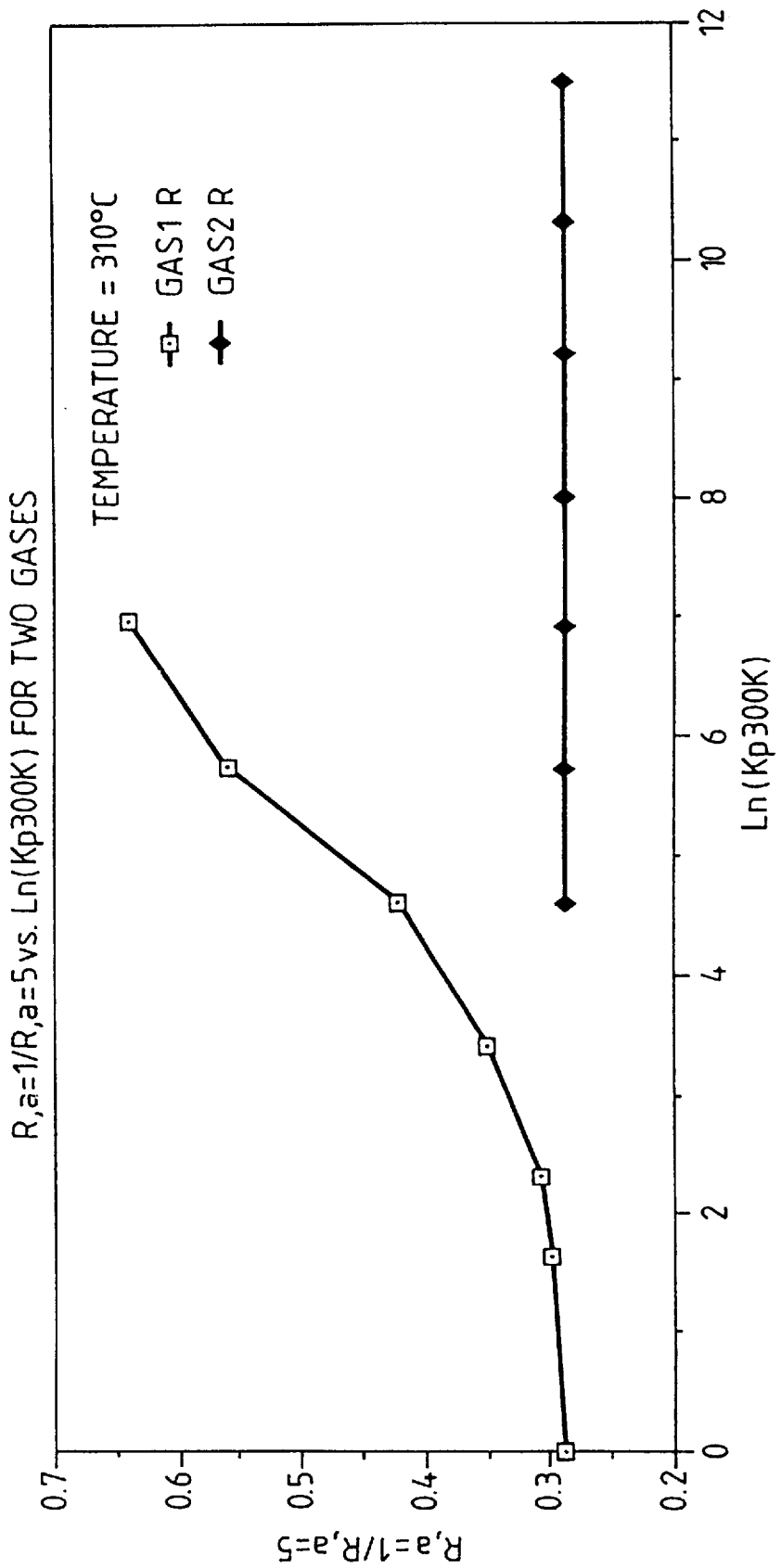
FIG. 4 shows, for the sensor of FIG. 1, the variation of the ratio of the resistance measured between widely spaced electrodes to that measured between closely spaced electrodes, as a function of gas concentration for reactive and unreactive gases.

Reference is now made to FIG. 4, in which the horizontal co-ordinate axis represents a natural logarithm of Kp, while the vertical axis represents the ratio of the resistance R, a=1 measured between the electrodes 3 and 4 to the resistance R, a=5 measured between the electrodes 2 and 3, where "a" (in arbitrary units) is one-half of the spacing between the electrodes concerned. FIG. 4 shows the variation of this ratio as a function (Kp) of the concentration of two gases, for the sensor of FIG. 1 at 31C. Gas 1 is a reactive gas such as carbon monoxide or hydrogen. Gas 2 is an unreactive gas such as methane. Both curves were obtained at the same temperature, so that KT is constant in both cases.

Figure 5:
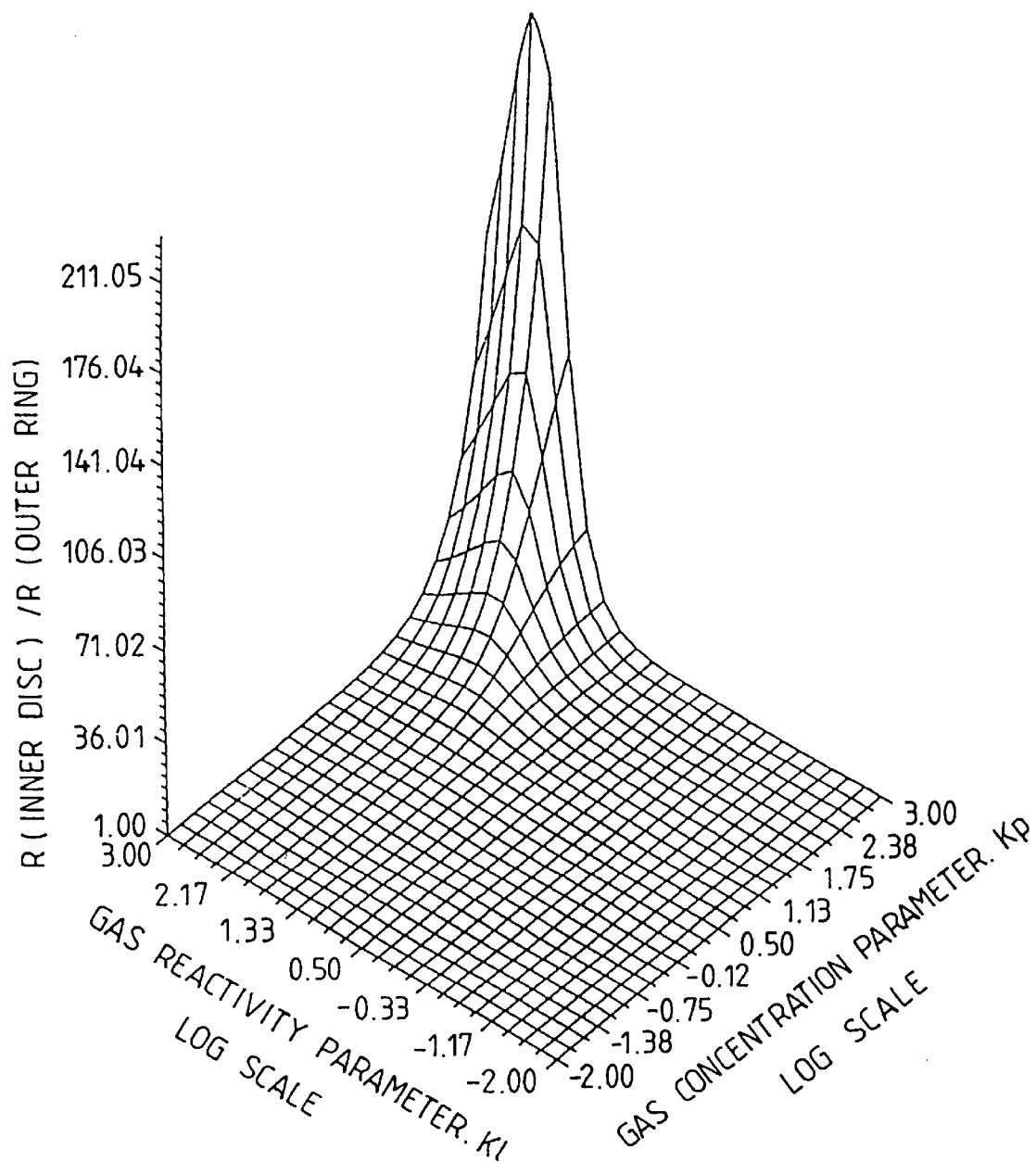
FIG. 5 shows, for the sensor of FIG. 2, a three-dimensional plot of the ratio of the resistance measured between a common electrode and an inner disc electrode to that measured between the common electrode and an outer ring electrode, as a function of gas concentration and temperature.

FIG. 5, on the other hand, shows for the sensor of FIG. 2 a three-dimensional plot of the ratio of the resistance (R [inner disc]) between the inner disc 23 and the common electrode 22 and the resistance (R [outer ring]) between the annular outer electrode 24 and the electrode 22, with variation of both the gas concentration parameter Kp and the gas reactivity or diffusion rate parameter KT.

Both FIGS. 4 and 5 show that, for unreactive gases (which have a low diffusion parameter KT), the ratio of resistances between the different pairs of electrodes is independent of gas concentration, whereas for reactive gases (which have a high diffusion parameter KT) the ratio of the resistances between the different pairs of electrodes varies considerably with the concentration of the gas. Any zero drift of the sensor is of course canceled out in the respective resistance ratios.

If a further number of electrodes at different spacings are used in a planar sensor (e.g. as in FIG. 1), or in different radial positions in a disc sensor (e.g. as in FIG. 2), then taking appropriate ratios will allow the measurement of multiple gases in mixtures to be made. This is because it will usually be possible, especially if use is also made of the possibility of varying the temperature, that one particular gas in the mixture has a composition gradient extending across the gas-sensitive part of the sensor, whereas the other gases in the mixture are either uniform in concentration throughout the gas-sensitive part of the sensor, or have a concentration which falls rapidly to zero at the outer surface of the sensing element.

Figure 6:
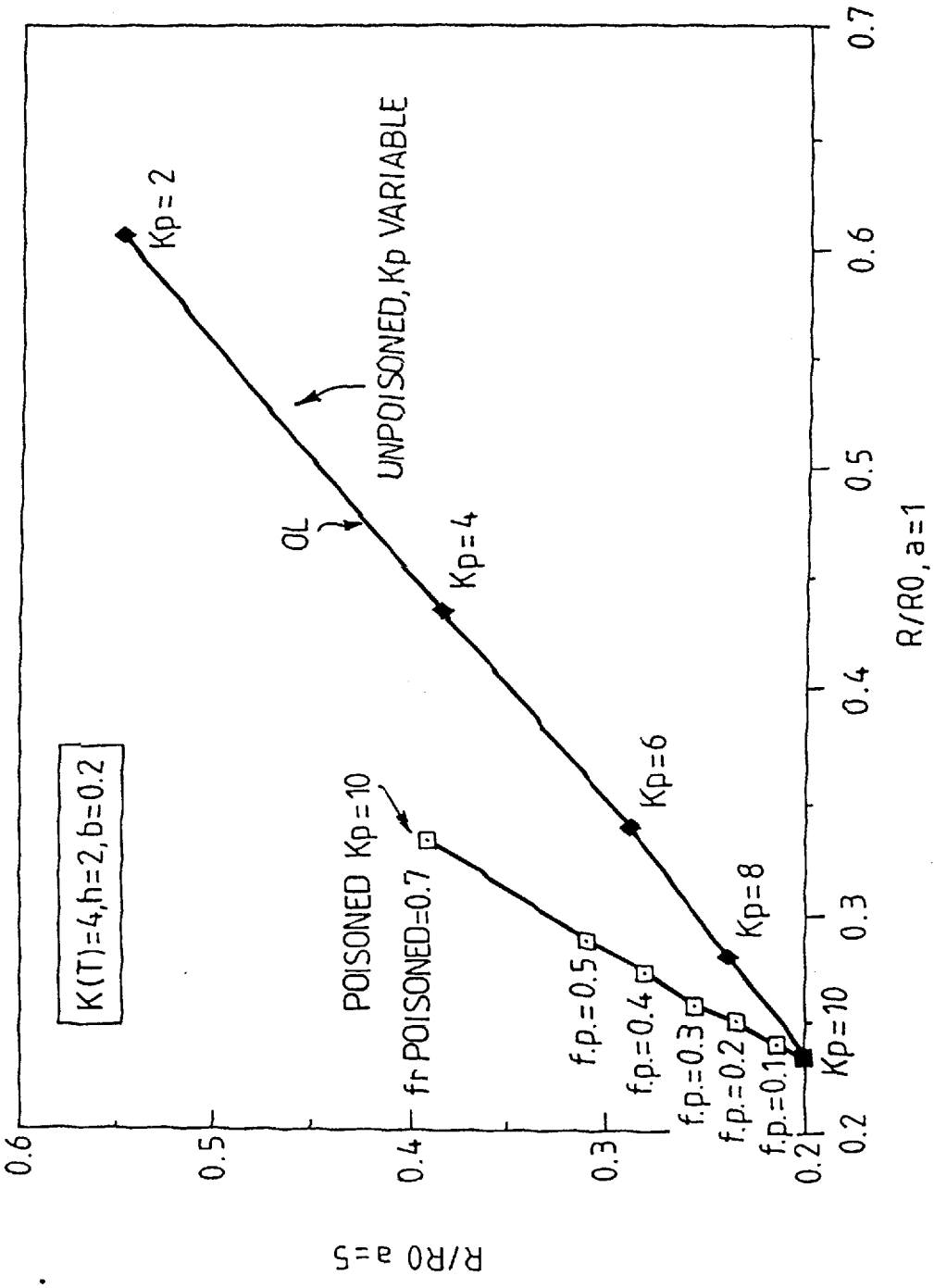
FIG. 6 is a plot, in respect of planar sensors as shown in FIG. 1, of the variable shown in FIG. 4 for a sensor which is working perfectly and one which is not; and, FIG. 7 shows diagrammatically a three-electrode sensor.

Reference is now made to FIG. 6, in which the vertical and horizontal co-ordinate axes represent, respectively, the resistance measured between the more widely-spaced electrodes 3 and 4 and the resistance measured between the closer electrodes 2 and 3. Each of these resistances is here represented as the ratio of the resistance R in the gas concerned to the corresponding resistance Ro in air, Ro being constant at a given temperature. The value of KT is fixed, as FIG. 6 refers to a single gas at a fixed sensor temperature.

FIG. 6 relates to a planar sensor such as that shown in FIG. 1. If the sensor is operating correctly, then the resistance between the two pairs of electrodes will move along the right-hand line shown as the concentration Kp of the reactive gas changes. This line may be referred to as the "operating line". If something other than the concentration of the reactive gas changes, then the measured operating point will move off the expected operating line and the operating line of the sensor as measured will change also.

Also shown in FIG. 6 is a line showing the effect of poisoning, where "fr POISONED" and "f. p." means "fraction poisoned". Here, for a given value of Kp, the sensing element of a sensor according to the invention has become poisoned to varying degrees such that, in the outer part of the sensing element extending inwardly from its surface through some fraction of its thickness, the reactive gas does not burn and the conductivity of the material of the sensing element may not respond to the presence of the reactive gas.

Thus, should a point defined by measured resistances be found to be off an operating line obtained under perfect conditions as a calibration curve, then there is indicated a change in conditions other than a change in the concentration of the reactive gas. Factors other than the poisoning of the sensitive element can cause such a change. These include drifts in the zero resistance of the sensor and the presence of reactive gases other than a specific reactive gas. The use of sensors according to the invention and the taking of repeated measurements to derive a measured operating line enables such changes, representing malfunctions of the sensor, to be distinguished from changes in the concentration of the specific reactive gas that is to be detected. This reduces the possibility of false alarms if a sensor is being used to monitor the composition of the given mixture, or can give an indication that a sensor has become faulty and needs to be changed. Thus the measured resistances R can be used to compare the relationship between them with the calibration curve, with a view to establishing the concentration of the gas to be measured, and with the facility to check the result for reliability.

Figure 7:
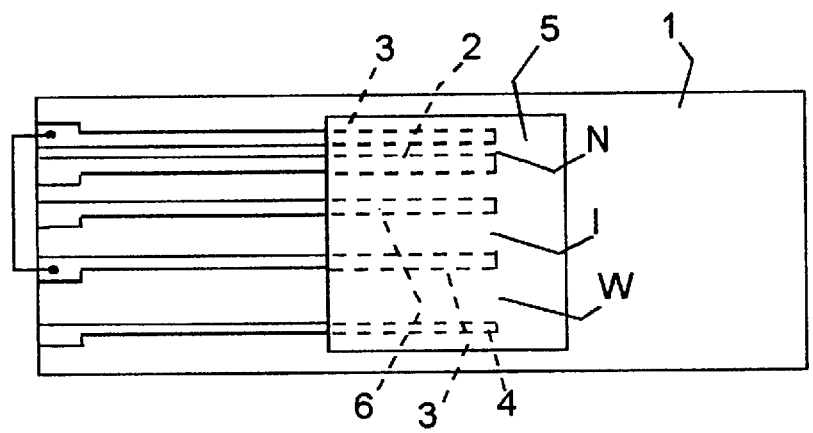

In circumstances where it is known that progressive sensor poisoning takes place, a more elaborate arrangement (shown in FIG. 7, which is a modified version of FIG. 1 (*a*)) enables the progression of the poisoning of the sensor to be followed, and a warning given when it is no longer performing usefully. Instead of two pairs of electrodes 2, 3 and 3, 4 as in FIG. 1, there are in this case three pairs of electrodes, namely a pair 2, 3, a pair 6, 3 and a pair 4, 3, with narrow, intermediate and wide spacings N, I and W respectively. There are now two operating lines, defined by "narrow/intermediate" and "narrow/wide" electrode spacing resistance ratios. Poisoning of the sensitive element will affect the narrow/wide operating line first, and the changes in this operating line will chart the progress of the poisoning. Eventually the narrow/intermediate operating line will begin to be affected. The onset of this change can be used to trigger a suitable warning device.

If three pairs of electrodes are used, then the three resistances define an operating surface instead of an operating line, and a measured operating point would move off this surface in the event of poisoning of the sensor.

It is evident that the above statements apply equally to the disc configuration of FIG. 2, with the inner disc 23 corresponding to the closer electrodes 2 and 3 of the planar version in FIG. 1, and with concentric ring electrodes of increasing radius then corresponding to progressively more widely-spaced electrodes of the planar version.

So far as the material of the sensitive layer is concerned, any of the materials listed above can be used. A particular material is chosen in relation to a specific reactive gas to be detected. For example, if it is desired to detect methane in air, then tin dioxide is a suitable material for the sensitive layer. Carbon monoxide in air may be detected also using tin dioxide for the sensitive layer.

What is claimed as invention is:

1. A method of determining the concentration of at least one gas in a gaseous mixture, using a gas sensor comprising: a body of material having an electrical conductivity sensitive to the presence of said at least one gas in said gaseous mixture, said body having an active surface, and a plurality of electrodes in contact with said body and defining at least two electrode pairs, each electrode pair consisting of two electrodes of said plurality of electrodes spaced apart, with the spacing between the electrodes of an electrode pair, or the distance between an electrode pair and an active surface, being different as between one said electrode pair and another, said method comprising the steps of:

(1) exposing the said active surface to a series of gaseous mixtures each having different known concentration of said at least one gas and wherein said at least one gas reacts on said active surface;

(2) measuring the electrical resistance between the electrodes of each said electrode pair, for each member of said series, thereby obtaining for each said electrode pair measured values of the resistance of that pair;

(3) creating a series of calibration values from parameters derived from said measured values, which series relates said parameters to said known concentrations of said at least one gas in the gaseous mixture;

(4) exposing the said active surface to the said gaseous mixture containing the said at least one gas whose concentration in the mixture it is wished to determine so that at least one gas reacts on said active surface;

(5) measuring the electrical resistance between the electrodes of each said electrode pair during step (4);

(6) comparing a parameter, derived from the said measured values of step (5), with said series of calibration values to determine the concentration of said at least one gas in the said gaseous mixture;

(7) creating, from the measurements of step (2), a calibration datum constituting at least one operating line or an operating surface under conditions when it is known that the sensor is not malfunctioning;

(8) comparing the measurements of step (5) with said calibration datum and using any deviation therebetween to indicate a malfunction of the sensor.

2. A method as claimed in claim 1, wherein, for each electrode pair, the said parameter is the ratio of the resistance of that pair in the presence of a said at least one gas to the resistance of the same pair in air.

3. A method as claimed in claim 1, wherein the said body defines at least three electrode pairs, and in each pair the electrodes are spaced apart by an amount different from that in the other two electrode pairs, step (2) being performed over a period of time, and step (6) further including the step of detecting any progressive increase in said deviation over said period of time.

4. A method as claimed in claim 1, further including the step of varying the operating temperature of the sensor, with each of at least steps (2) and (6) being performed at different temperatures so as to detect a different gaseous medium in a gaseous mixture to which said active surface is exposed.

5. A method as claimed in claim 1, wherein at least one of said electrodes is common to more than one of said electrode pairs.

6. A method as claimed in claim 5, wherein the common electrode is disposed asymmetrically in relation to an electrode of one electrode pair and an electrode of another electrode pair.

7. A method as claimed in claim 5, wherein said sensor is of planar configuration, said body being generally planar with said electrodes disposed in contact with a flat surface of said body.

8. A method as claimed in claim 5, wherein said sensor is of cylindrical configuration, said body being generally cylindrical with said electrodes disposed in contact with a cylindrical surface of said body.

9. A method as claimed in claim 5, wherein said electrically conductive body is in the form of a porous disc, with an electrode, common to each said electrode pair, formed over one planar surface, a central disc electrode of one pair on its other planar surface, and an annular electrode of another pair surrounding the central disc electrode and concentric with it.

10. A method as claimed in claim 5, wherein said body is made of at least one semiconducting metal oxide ceramic material.

11. A method as claimed in claim 5, wherein said body has a thin coating of a catalytic material suitable for catalyzing at least one type of reaction in the group consisting of combustion and decomposition reactions.

* * * * *